(12) United States Patent
Lewis et al.

(10) Patent No.: US 8,431,408 B2
(45) Date of Patent: Apr. 30, 2013

(54) HANDHELD DIABETES MANAGING DEVICE WITH LIGHT PIPE FOR ENHANCED ILLUMINATION

(75) Inventors: Joseph B. Lewis, Indianapolis, IN (US); Michael F DeRossi, Lidenhurst, IL (US); Blaine Edward Ramey, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 379 days.

(21) Appl. No.: 12/905,508

(22) Filed: Oct. 15, 2010

(65) Prior Publication Data

US 2012/0095316 A1    Apr. 19, 2012

(51) Int. Cl.
*G01N 21/00*    (2006.01)
*G01N 33/48*    (2006.01)
*G01N 21/77*    (2006.01)
*G01N 21/75*    (2006.01)

(52) U.S. Cl.
USPC ........... 436/164; 436/169; 422/401; 422/404; 422/420; 422/68.1; 422/82.05; 422/82.11

(58) Field of Classification Search .................. None
See application file for complete search history.

(56) References Cited

U.S. PATENT DOCUMENTS

| | | |
|---|---|---|
| 6,514,460 B1 | 2/2003 | Fendrock |
| 6,659,966 B2 | 12/2003 | Essenpreis |
| 7,731,900 B2 | 6/2010 | Haar et al. |
| 2003/0157724 A1* | 8/2003 | Petrich et al. ............ 436/164 |
| 2003/0168998 A1 | 9/2003 | Cristoni et al. |
| 2004/0092994 A1 | 5/2004 | Briggs et al. |
| 2005/0009126 A1 | 1/2005 | Andrews et al. |
| 2005/0023137 A1 | 2/2005 | Bhullar et al. |
| 2005/0201897 A1 | 9/2005 | Zimmer et al. |
| 2005/0232815 A1 | 10/2005 | Ruhl et al. |
| 2005/0265094 A1 | 12/2005 | Harding et al. |
| 2005/0276133 A1 | 12/2005 | Harding et al. |
| 2006/0100655 A1 | 5/2006 | Leong et al. |
| 2009/0227855 A1 | 9/2009 | Hill et al. |
| 2010/0137698 A1 | 6/2010 | Andrews et al. |

FOREIGN PATENT DOCUMENTS

| | | |
|---|---|---|
| EP | 1199978 A2 | 5/2002 |
| EP | 1312308 A1 | 5/2003 |
| EP | 1578272 A1 | 9/2005 |
| EP | 1652474 A2 | 5/2006 |
| WO | WO-0108551 A2 | 2/2001 |
| WO | WO-2004041082 A1 | 5/2004 |
| WO | WO-2004047642 A1 | 6/2004 |
| WO | WO-2005012900 A1 | 2/2005 |
| WO | WO-2005119234 A2 | 12/2005 |
| WO | WO 2010/075157 | 7/2010 |
| WO | WO2011/015353 | 2/2011 |

* cited by examiner

*Primary Examiner* — Neil N Turk
(74) *Attorney, Agent, or Firm* — Harness, Dickey (57) ABSTRACT

A handheld diabetes management device for providing enhanced illumination includes a housing with an access port and a light aperture. The housing further includes a coupling member on an inner surface thereof. Furthermore, the device includes a measurement engine housed within the housing and communicating with the access port for analyzing body fluid disposed on a dosing area of a diabetes test element. Also, the device includes a circuit board communicating with the measurement engine. The device further includes a light source mounted to the circuit board and a light pipe coupled to the housing via the coupling member. The light pipe is disposed adjacent the light source to receive light from the light source travelling in a first direction. The light pipe redirects the light along a second direction to be emitted out of the housing through the light aperture toward the dosing area of the diabetes test element.

20 Claims, 5 Drawing Sheets

HANDHELD DIABETES MANAGING DEVICE WITH LIGHT PIPE FOR ENHANCED ILLUMINATION

FIELD

The present disclosure relates to a handheld diabetes managing device and, more particularly, relates to a handheld diabetes managing device with a light pipe for enhanced illumination of a test element.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise and lifestyle. Lab test results include HbAlC, cholesterol, triglycerides, and glucose tolerance. Healthcare professional recommendations include prescriptions, diets, test plans, and other information relating to the patient's treatment.

There are times in which the diabetes patient may wish to perform personal glucose testing in low light conditions. For instance, the patient may want to perform the test in a dark or poorly lit room. Because the test requires a certain amount of precision (e.g., proper placement of a blood droplet on the dosing area of a test strip), it can be difficult to complete the test in such conditions. Thus, there is a need for a handheld diabetes management device for providing enhanced illumination in such situations.

SUMMARY

This section provides a general summary of the disclosure, and is not a comprehensive disclosure of its full scope or all of its features.

A handheld diabetes management device for providing enhanced illumination on a dosing area of a diabetes test element is disclosed. The diabetes management device includes a housing with a light aperture and an access port for the diabetes test element. The light aperture is formed on a sidewall of the housing. The light aperture and the access port are separated by a portion of the housing. The housing further includes a coupling member on an inner surface thereof. The device also includes a measurement engine housed within the housing and communicating with the access port for analyzing a body fluid disposed on the dosing area of the diabetes test element. Moreover, the device includes a circuit board housed within the housing and communicating with the measurement engine. Still further, the device includes a light source mounted to the circuit board and a light pipe that is coupled to the housing via the coupling member. The light pipe is disposed adjacent the light source to receive light from the light source travelling in a first direction, and the light pipe redirects the light along a second direction to be emitted out of the housing through the light aperture toward the dosing area of the diabetes test element. The second direction is at a nonzero angle relative to the first direction. Additionally, in some embodiments, the circuit board includes a control processor, and the light source operably communicates with the control processor to provide a visual feedback signal indicating a status of the body fluid analysis. The light pipe transmits the visual feedback signal through the light aperture. Also, in some embodiments, the light pipe includes a first portion and a second elongated portion having a distal end adjacent the light aperture of the housing. The first portion has a first surface facing the light source for receiving light from the light source and a substantially flat reflecting surface at a nonzero angle relative to the first surface. The reflecting surface reflects the light received from the first surface toward the second elongated portion and directs the light out of the housing via the light aperture, such that the light illuminates only the blood dosing area on the test element.

Moreover, a method of providing enhanced illumination on a dosing area of a diabetes test element of a handheld diabetes management device is disclosed. The method includes providing the handheld diabetes management device having a housing. The housing includes a light aperture and an access port for the diabetes test element. The light aperture is formed on a sidewall of the housing, and the light aperture and the access port are separated by a portion of the housing. The housing further includes a coupling member on an inner surface thereof. The handheld diabetes management device also includes a measurement engine housed within the housing and communicating with the access port for analyzing a body fluid disposed on the dosing area of the diabetes test element. The handheld diabetes management device additionally includes a circuit board housed within the housing and communicating with the measurement engine. The handheld diabetes management device further includes a light source mounted to the circuit board, and the handheld diabetes management device also includes a light pipe that is coupled to the housing via the coupling member. The light pipe is disposed adjacent the light source. The method further includes illuminating the light source such that the light pipe receives light from the light source travelling in a first direction. Also, the method includes redirecting the light with the light pipe along a second direction to be emitted out of the housing through the light aperture toward the dosing area of the diabetes test element. The second direction is at a nonzero angle relative to the first direction.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
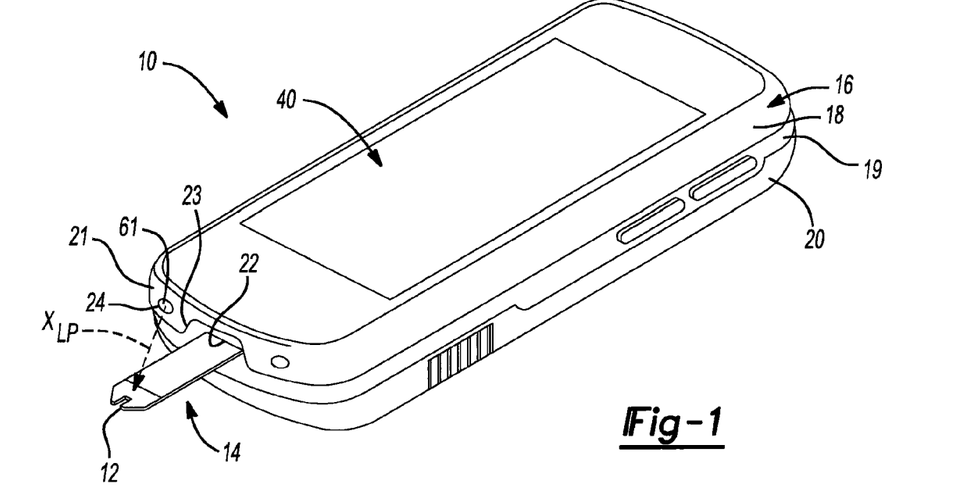
FIGS. 1 and 2 are exemplary perspective views of a handheld diabetes managing device according to the present teachings.
Figure 2:
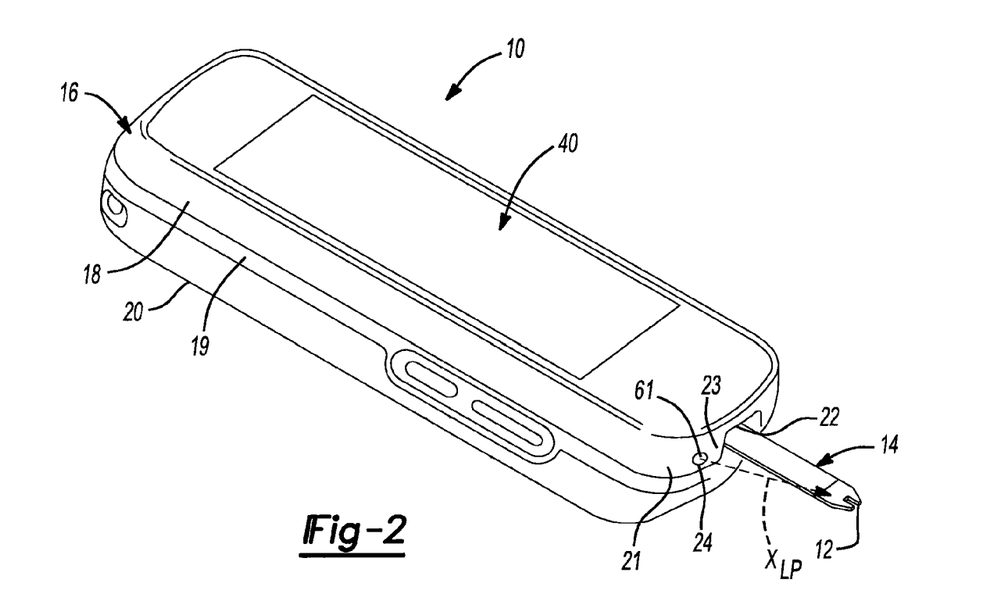

Referring initially to FIGS. 1 and 2, an exemplary embodiment of a portable, handheld diabetes management device 10 is illustrated according to the present teachings. The diabetes management device 10 can be used for analyzing a body fluid disposed on a dosing area 12 of a diabetes test element 14. For instance, as will be discussed, the test element 14 can be a disposable glucose test strip of a known type. A droplet of blood can be applied to the dosing area 12 while the test element 14 is inserted within the device 10, and the device 10 can analyze the droplet to detect the blood glucose level therein. It will be appreciated, however, that the device 10 could be used for analyzing any other suitable characteristic of any other body fluid without departing from the scope of the present disclosure.

The device 10 can include a housing 16. The housing 16 can include a first portion 18, an elongate second portion 20, and a center portion 19. The first, center, and second portions 18, 19, 20 can be removably coupled together such that the center portion 19 is disposed between the first and second portions 18, 20, to define an interior space therebetween, and to house various components therein, as will be discussed below.

Moreover, the housing 16 can include and can define an access port 22. The access port 22 can be a slot that is defined in the center portion 19. The access port 22 can removably receive the test element 14 as will be discussed below.

The housing 16 can include a light aperture 24. In some embodiments, the light aperture 24 can be a through hole with an ovate shape extending through a sidewall 21 of the first portion 18 of the housing 16. Furthermore, the light aperture 24 can be adjacent the access port 22; however, the light aperture 24 can be separated at a distance from the access port 22. Specifically, the light aperture 24 and the access port 22 can be separated by an intervening portion 23 of the sidewall 21 of the first portion 18 of the housing 16 such that the light aperture 24 and access port 22 are completely separate and distinct from each other.

Figure 3:
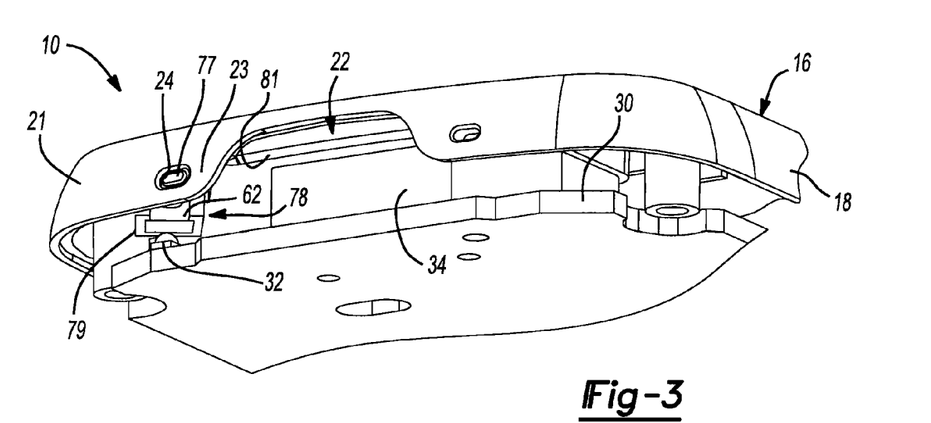
FIG. 3 is a perspective view of a portion of interior components of the handheld diabetes managing device of FIGS. 1 and 2 according to exemplary embodiments of the present teachings.
Figure 4:
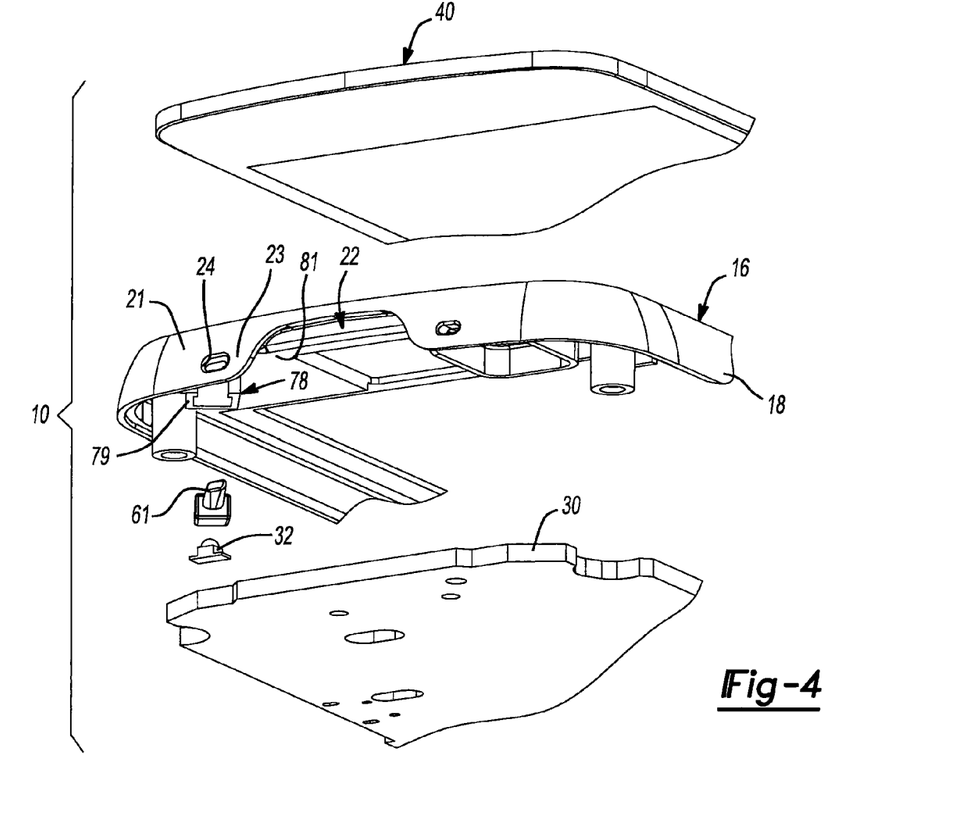
FIG. 4 is a perspective, exploded view of the interior components of FIG. 3.
Figure 7:
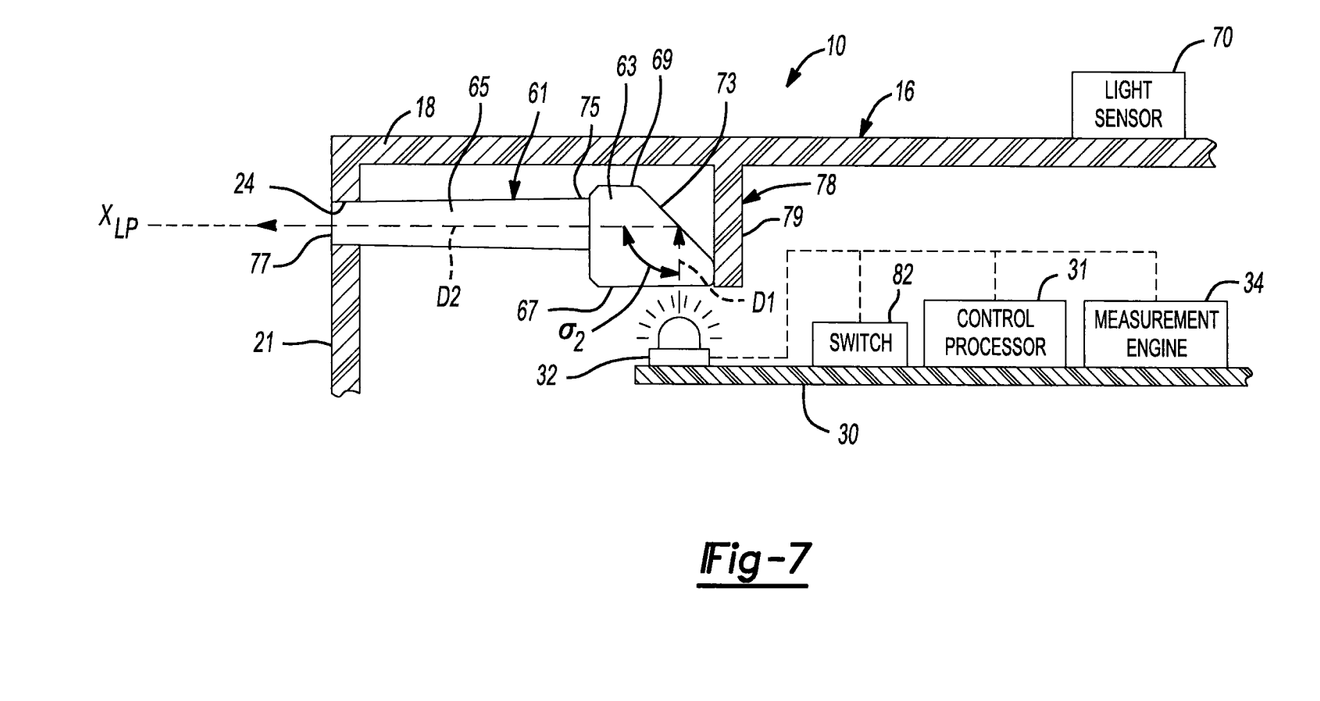
FIG. 7 is a section view of the light pipe shown in operation.

Referring now to FIGS. 3, 4, and 7, various internal components that are housed by the housing 16 will be discussed. For instance, the device 10 can include a circuit board 30. The circuit board can be a printed circuit board with various circuits and circuit components included thereon. For instance, as shown in FIG. 7, a control processor 31 can be included on the circuit board 30 for controlling various functions of the device 10 as will be discussed. Furthermore, a light source 32 (FIGS. 3, 4, and 7) can be mounted to the circuit board 30. The light source 32 can be of any suitable type, such as a light emitting diode (LED). The circuit board 30, the control processor 31, and the light source 32 can each be housed within the housing 16.

The device 10 can additionally include a measurement engine 34 (FIGS. 3 and 7). The measurement engine 34 can be of a known type for analyzing the body fluid applied to the test element 14 as discussed above. The measurement engine 34 can be operably mounted to the circuit board 30 and can communicate with the access port 22. As such, when the test element 14 is inserted within the access port 22 and the body fluid is applied, the measurement engine 34 can perform the predetermined analysis. Moreover, the measurement engine 34 can include associated software and logic (e.g., within the control processor 31) for performing and controlling the analysis of the body fluid.

As shown in FIGS. 1, 2, and 4 the device 10 can include a display 40. The display 40 can be operably connected to the control processor 31 for displaying various information (e.g., text, graphics, icons, and other objects) relating to the operation of the device 10. The display 40 can be operably supported by the first portion 18 of the housing 16.

Referring now to FIGS. 3-7, the device 10 will be discussed in additional detail. As shown, the device 10 can additionally include a light pipe 61. The light pipe 61 can be made out of or include a light transmissive material. For instance, the light pipe 61 can be made out of or include a rigid, polymeric, light transmissive material. In other embodiments, the light pipe 61 can be made out of or include a flexible, light transmissive material.

Figure 5:
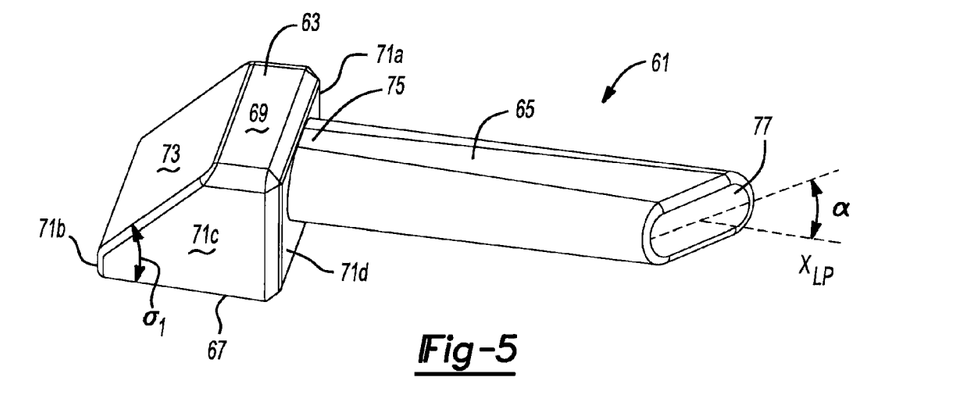
FIGS. 5 and 6 are various perspective views of a light pipe of the handheld diabetes managing device of FIGS. 1 and 2.
Figure 6:
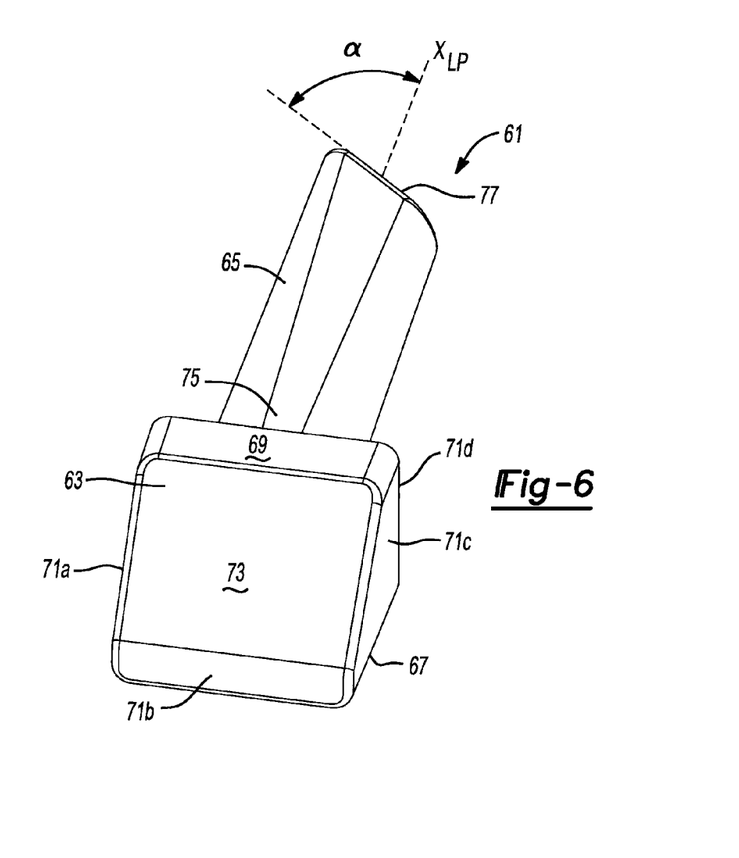

As shown in FIGS. 5-7, the light pipe 61 can generally include a first portion 63 and a second portion 65. The first and second portions 63, 65 can be integrally connected so as to be monolithic.

The first portion 63 can be a block with substantially flat surfaces and with chamfered edges. For instance, the first portion 63 can include a first surface 67 (FIG. 7) and a second surface 69 that are opposite and substantially parallel to each other. The first portion 63 can also include a plurality of side surfaces 71a-71d that each extend substantially perpendicular to the first and second surfaces 67, 69. The side surfaces 71a, 71c can be opposite and substantially parallel to each other. The side surfaces 71b, 71d can be opposite and substantially parallel to each other. Moreover, the first portion 63 can include a reflecting surface 73 that extends between the second surface 69 and the side surface 71b. The reflecting surface 73 can be substantially flat and disposed at an acute angle $\theta_1$ relative to the first surface 67. As will be discussed, the angle $\theta_1$ can be selected so that light transmitted through the first portion 63 can reflect off of the reflecting surface 73 toward the second portion 65 and along an axis $X_{LP}$ of the second portion 65.

The second portion 65 can be substantially elongate, tubular, and can have a substantially straight longitudinal (second) axis $X_{LP}$. The second portion 65 can have a rounded (e.g., circular or ovate) or rectangular cross section taken perpendicular to the longitudinal axis $X_{LP}$. The second portion 65 can also include a proximal end 75, which is connected directly to the side surface 71d of the first portion 63, and a distal end 77 that is opposite and spaced apart from the proximal end 75. As shown, the second portion 65 can be tapered between the proximal and distal end 75, 77. Also, the distal end 77 can be substantially flat and can be beveled so as to define a plane that is disposed at an acute angle $\alpha$ relative to the longitudinal axis $X_{LP}$ (FIGS. 5 and 6).

It will be appreciated that the first and second portions 63, 65 of the light pipe 61 can have any other suitable shape. For instance, the first portion 63 can have one or more rounded (convex or concave) outer surfaces. Moreover, the second portion 65 can have a non-linear longitudinal axis $X_{LP}$ and/or can any number of flat surfaces in cross section. Furthermore, the distal end 77 can have convex or concave curvature (e.g., to function as a lens for focusing light transmitted through the light pipe 61).

The light pipe 61 can be coupled to the housing 16 as shown in FIGS. 3 and 4. For instance, the housing 16 can include a coupling member 78 for retaining the light pipe 61. In some embodiments, the coupling member 78 can include a plurality of thin, integrally coupled walls 79 that extend from an inner surface 81 of the first portion 18 of the housing 16 toward the circuit board 30. As shown in FIG. 3, the light pipe 61 can be received between the walls 79 to be retained therebetween. The walls 79 can be shaped and sized so as to define a recess that closely matches the outer periphery of the light pipe 61. In some embodiments, the light pipe 61 can be retained between the walls 79 by friction, by an interference fit, by adhesives, by a fastener, or in any other manner.

When the light pipe 61 is mounted to the housing 16, the first surface 67 can be exposed from the walls 79 of the first portion 18 of the housing 16 (FIG. 3). Also, when the light pipe 61 is mounted, the first surface 67 can be disposed adjacent the light source 32 such that the first surface 67 directly faces the light source 32 (FIGS. 3 and 7).

Furthermore, when the light pipe 61 is mounted to the housing 16, the distal end 77 of the second portion 65 can be disposed adjacent the light aperture 24. For instance, the distal end 77 can be exposed from the housing 16 via the light aperture 24. Also, it will be appreciated that the distal end 77 can be angled with respect to the longitudinal axis $X_{LP}$ such that the distal end 77 is substantially flush with the area of the housing 16 surrounding the light aperture 24.

During operation, as shown in FIG. 7, light from the light source 32 can be emitted toward the light pipe 61 in a first direction D1 (e.g., substantially perpendicular to the first surface 67. The first surface 67 can receive the light traveling in the first direction D1 and transmit the light toward the reflecting surface 73. The light can reflect from the reflecting surface 73 and be redirected toward a second direction D2. The second direction D2 can be at a nonzero angle $\theta_2$ relative to the first direction D1. For instance, in some embodiments, the angle $\theta_2$ can be approximately ninety degrees (90°). Once the light is redirected toward the second direction D2, the light can travel along (e.g., substantially parallel to) the longitudinal axis $X_{LP}$ and out of the distal end 77 of the light pipe 61. Thus, the light pipe 61 can efficiently transmit the light generated by the light source 32 out of the housing 16 through the light aperture 24. In some embodiments, because the taper of the second portion 65 of the light pipe 61, the transmitted light can be concentrated as it travels through the second portion 65.

Also as shown in FIGS. 1 and 2, the light pipe 61 can be disposed such that the longitudinal axis $X_{LP}$ is substantially directed toward and aligned with the dosing area 12 of the test element 14. As such, the light transmitted from the light pipe 61 can illuminate the dosing area 12 as represented by an arrow in FIGS. 1 and 2. In some embodiments, the light pipe 61 can be focused on the dosing area 12 to distinguish the dosing area 12 from other portions of the test element 14 (e.g., only the dosing area 12 of the test element 14 is illuminated by the light pipe 61). As such, the user can more easily recognize where to apply a blood droplet for glucose analysis, and proper application of the blood droplet to the dosing area 12 is more likely.

It will also be appreciated that the device 10 can provide enhanced illumination efficiently and cost effectively. The light pipe 61 can be relatively inexpensive. The circuit board 30 can be manufactured independently with the light source 32 included thereon before being assembled within the housing 16. Then, during assembly of the device 10, the light pipe 61 can be easily mounted to the housing 16, and the circuit board 30 can be housed within the housing 16, such that the light pipe 61 is in its proper position for receiving light from the light source 32. The light pipe 61 is then ready for transmitting light out of the housing 16 toward the test element 14.

In some embodiments, the control processor 31 can control the light source 32 such that the light source 32 provides a visual feedback signal. The visual feedback signal (i.e., the light from the light source 32) can be transmitted through the light pipe 61.

The visual feedback signal can be of any suitable type. For instance, the light source 32 can be controlled such that the light emitted by the light source 32 changes colors (e.g., from blue light to red light, etc.). Also, the light source 32 can be controlled such that the light is emitted in a predetermined pattern, and the pattern can change to provide feedback. Specifically, the light source 32 can be illuminated for a predetermined amount of time, and then the light source 32 can begin blinking, and/or the blinking can speed up or slow down to provide visual feedback.

The feedback signal can be provided for any suitable purpose. For instance, the feedback signal can inform the user that the glucose analysis has been performed successfully, or that there has been an error in performing the glucose analysis. Also, the feedback signal can inform the user that the test element 14 is faulty and/or is not communicating properly with the measurement engine 34. Still further, the feedback signal can inform the user of the results of the analysis (e.g., high glucose level, low glucose level, and/or satisfactory glucose level). It will be appreciated that this visual feedback can be provided in addition to or as an alternative to audible feedback provided by the speaker of the device 10 and/or by messages or other objects displayed on the display 40.

Additionally, as shown schematically in FIG. 7, the device 10 can include a switch 82 that selectively turns the light source 32 on and off. The switch 82 can be of any suitable type, such as a mechanical switch (e.g., displaceable button, slider, etc.), an electronic switch, and the like. Furthermore, the switch 82 can automatically turn the light source 32 on and off in response to other events. For instance, the light source 32 can turn on automatically when the device 10 is powered up. Also, the light source 32 can be operably coupled to an ambient light sensor 70, such as a photocell or other similar device, and when ambient light levels are below a predetermined limit, the switch 82 can automatically illuminate the light source 32. In still other embodiments, the light source 32 can automatically illuminate upon insertion of the test element 14 into the access port 22. The switch 82 can be designed such that the device 10 can conserve energy.

Figure 8:
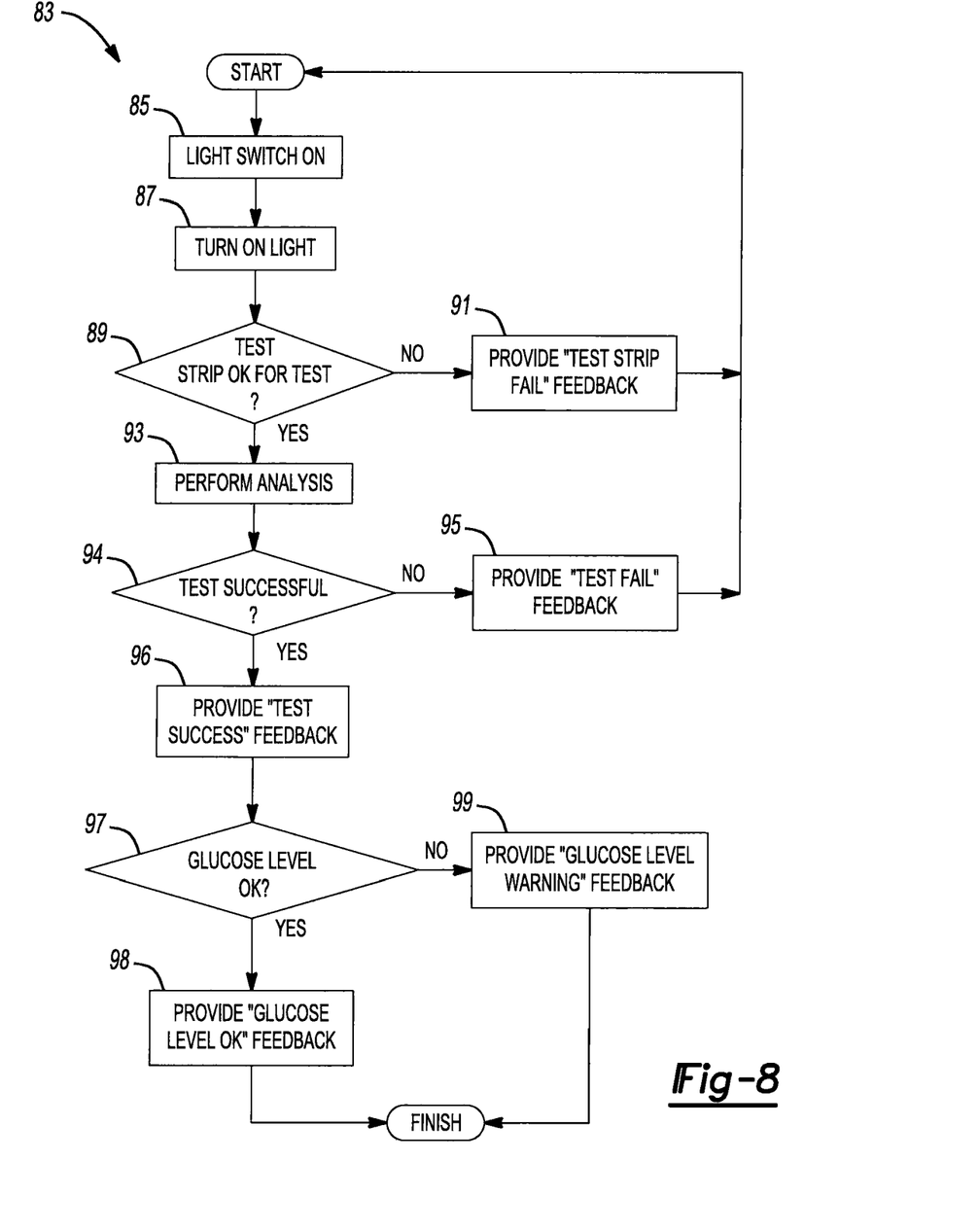
FIG. 8 is a flow chart illustrating a method of operation of the handheld diabetes managing device according to various exemplary embodiments.

Referring now to FIG. 8, a method 83 of operating the light pipe 61 of the device 10 is illustrated according to various exemplary embodiments. As shown, the method 83 can begin at block 85, wherein the switch 82 is changed from OFF to ON. As discussed above, the switch 82 can automatically and/or manually turn ON. The method 83 continues in block 87, wherein the light source 32 begins to illuminate.

Then, in decision block 89, it is determined whether the test element 14 is satisfactory for performing the glucose analysis. For instance, if the test element 14 is inserted improperly, if the test element 14 is defective, etc. (decision block 89 answered negatively), then block 91 follows. In block 91, the control processor 31 causes the light source 32 to provide a "test strip fail" feedback signal. As mentioned above, this feedback signal can be a change in color, illumination pattern, etc., informing the user that the test element 14 needs to be replaced before the analysis can be performed. Subsequently, the method 83 can restart until a new test element 14 is replaced and is satisfactory for performing the analysis.

If there is no problem with the test element 14 (decision block 89 answered affirmatively), then the glucose analysis can be performed in block 93. As mentioned above, the light from the light pipe can illuminate and distinguish the dosing area 12 of the test element 14 to help guide the user, even in low ambient light conditions.

Next, in decision block 94, it is determined whether the measurement engine 34 has successfully analyzed the blood on the test element 14. If not (decision block 94 answered negatively), then block 95 follows, and the control processor 31 causes the light source 32 to provide a "test fail" feedback signal. This signal can be different (e.g., in light color, light pattern, etc.) from the signal provided in block 91. Subsequently, the method 83 can restart until the test is performed successfully.

However, if the test is successful (decision block 94 answered affirmatively), then the control processor 31 can cause the light source 32 to provide a "test success" feedback signal in block 96. Again, this signal can be different than the other feedback signals discussed above.

Subsequently, in decision block 97, it can be determined whether the detected glucose level is within a satisfactory range. If the glucose level is within this range (decision block 97 answered affirmatively), then a "satisfactory" feedback signal can be output in block 98. This feedback signal can be different than each of the feedback signals discussed above in blocks 91 and 95. Moreover, if the detected glucose is either above or below this satisfactory range (decision block 97 answered negatively) one or more feedback signals can be provided at block 99. It will be appreciated that a "high detected glucose level" feedback signal can provided if the detected glucose level is above the satisfactory range, and a "low detected glucose level" feedback signal can be provided if the detected level is below the satisfactory range. The "high" and "low" feedback signals can be different from each other and can be different from each of the other feedback signals of blocks 91, 95, and 98.

Thus, the light pipe 61 and associated components of the device 10 can assist the user in performing analyses, especially in low ambient light conditions. Furthermore, the device 10 can provide various types of feedback to further assist the user.

What is claimed is:

1. A handheld diabetes management device for providing enhanced illumination on a dosing area of a diabetes test element, the diabetes management device comprising:
    a housing including a light aperture and an access port for the diabetes test element, the light aperture formed on a sidewall of the housing, the light aperture and the access port being separated by a portion of the housing, the housing further including a coupling member on an inner surface thereof;
    a measurement engine housed within the housing and communicating with the access port for analyzing a body fluid disposed on the dosing area of the diabetes test element;
    a circuit board housed within the housing and communicating with the measurement engine;
    a light source coupled to the housing; and
    a light pipe that is coupled to the housing via the coupling member, the light pipe disposed adjacent the light source to receive light from the light source travelling in a first direction, the light pipe redirecting the light along a second direction to be emitted out of the housing through the light aperture toward the dosing area of the diabetes test element, the second direction being at a nonzero angle relative to the first direction.

2. The handheld diabetes management device of claim 1, wherein the light pipe includes a first portion and an elongate second portion, the first portion disposed adjacent the light source, and the second portion including a distal end that is adjacent the light aperture to be exposed from the housing through the light aperture.

3. The handheld diabetes management device of claim 2, wherein the first portion includes a first surface that faces the light source and a reflecting surface, the light traveling through the first portion in the first direction from the first surface to the reflecting surface and reflecting off of the reflecting surface to be redirected toward the second direction.

4. The handheld diabetes management device of claim 3, wherein the reflecting surface is substantially flat.

5. The handheld diabetes management device of claim 2, wherein the distal end is substantially flat.

6. The handheld diabetes management device of claim 5, wherein the second portion defines a second axis and the distal end defines a plane that is disposed at an acute angle relative to the second axis.

7. The handheld diabetes management device of claim 2, wherein the second portion has a substantially straight longitudinal axis.

8. The handheld diabetes management device of claim 1, wherein the second direction is disposed at approximately a ninety degree (90°) angle relative to the first direction.

9. The handheld diabetes management device of claim 1, wherein the coupling member includes a plurality of walls that are integrally connected to the inner surface of the housing, the plurality of walls projecting from the inner surface toward the circuit board, the light pipe being mountably received between the plurality of walls.

10. The handheld diabetes management device of claim 1, wherein the light source provides a visual feedback signal relating to the analysis of the body fluid on the diabetes test element, and wherein the light pipe transmits the visual feedback signal through the light aperture.

11. The handheld diabetes management device of claim 10, wherein the visual feedback signal includes at least one of a change of color of the light and a change in illumination pattern of the light.

12. A method of providing enhanced illumination on a dosing area of a diabetes test element of a handheld diabetes management device, the method comprising:
   providing the handheld diabetes management device having a housing, the housing including a light aperture and an access port for the diabetes test element, the light aperture formed on a sidewall of the housing, the light aperture and the access port being separated by a portion of the housing, the housing further including a coupling member on an inner surface thereof, the handheld diabetes management device also including a measurement engine housed within the housing and communicating with the access port for analyzing a body fluid disposed on the dosing area of the diabetes test element, the handheld diabetes management device additionally including a circuit board housed within the housing and communicating with the measurement engine, the handheld diabetes management device further including a light source, the handheld diabetes management device also including a light pipe that is coupled to the housing via the coupling member, the light pipe disposed adjacent the light source;
   illuminating the light source such that the light pipe receives light from the light source travelling in a first direction; and
   redirecting the light with the light pipe along a second direction to be emitted out of the housing through the light aperture toward the dosing area of the diabetes test element, the second direction being at a nonzero angle relative to the first direction.

13. The method of claim 12, further comprising providing a visual feedback signal relating to the analysis of the body fluid on the diabetes test element, and transmitting the visual feedback signal through the light aperture.

14. The method of claim 13, wherein providing the visual feedback signal includes at least one of a changing a color of the light and changing an illumination pattern of the light.

15. The method of claim 13, wherein providing the visual feedback signal includes providing the visual feedback signal relating to at least one of whether the diabetes test element is sufficient for analyzing the body fluid, whether the measurement engine successfully analyzed the body fluid, and whether a detected glucose level of the body fluid is within a satisfactory range.

16. The method of claim 12, wherein the light pipe includes a first portion and an elongate second portion, the first portion disposed adjacent the light source, and the second portion including a distal end that is adjacent the light aperture to be exposed from the housing through the light aperture, wherein the first portion includes a first surface that faces the light source and a reflecting surface, and wherein redirecting the light includes reflecting the light off of the reflecting surface to be redirected toward the second direction.

17. The method of claim 16, wherein the reflecting surface is substantially flat.

18. The method of claim 12, wherein redirecting the light with the light pipe along the second direction includes redirecting the light along a substantially straight axis.

19. The method of claim 12, wherein directing the light with the light pipe along the second direction includes redirecting the light at approximately a ninety degree (90°) angle relative to the first direction.

20. A handheld diabetes management device for providing enhanced illumination comprising:
   a housing including an access port for a diabetes test element and a light aperture, the light aperture and the access port being separated by a portion of the housing;
   a measurement engine housed within the housing and communicating with the access port for analyzing a body fluid placed on a dosing area of the diabetes test element;
   a circuit board with a control processor housed within the housing and operably communicating with the measurement engine;
   a light source mounted inside the housing and operably communicating with the control processor to provide a visual feedback signal indicating a status of the body fluid analysis; and
   a light pipe mounted inside the housing opposite to the circuit board, the light pipe including a first portion and a second elongated portion having a distal end adjacent the light aperture of the housing, the first portion having a first surface facing the light source for receiving light from the light source and a substantially flat reflecting surface at a positive angle relative to the first surface, the reflecting surface reflecting the light received from the first surface toward the second elongated portion and directing the light out of the housing via the light aperture, such that the light illuminates only a blood dosing area on the test element, the light pipe transmitting the visual feedback signal through the light aperture.

* * * * *